US008022704B2

(12) United States Patent
Qian et al.

(10) Patent No.: US 8,022,704 B2
(45) Date of Patent: *Sep. 20, 2011

(54) METHOD FOR PRODUCING A MAGNETIC RESONANCE IMAGE OF AN OBJECT HAVING A SHORT $T_2$ RELAXATION TIME

(75) Inventors: Yongxian Qian, Pittsburgh, PA (US); Fernando E. Boada, Wexford, PA (US)

(73) Assignee: University of Pittsburgh-Of The Commonwealth System of Higher Education, Pittsburgh, PA (US)

( * ) Notice: Subject to any disclaimer, the term of this patent is extended or adjusted under 35 U.S.C. 154(b) by 17 days.

This patent is subject to a terminal disclaimer.

(21) Appl. No.: 12/784,528

(22) Filed: May 21, 2010

(65) Prior Publication Data
US 2010/0231218 A1   Sep. 16, 2010

Related U.S. Application Data

(63) Continuation of application No. 12/054,052, filed on Mar. 24, 2008, now Pat. No. 7,750,632.

(60) Provisional application No. 60/896,465, filed on Mar. 22, 2007.

(51) Int. Cl.
*G01V 3/00* (2006.01)
(52) U.S. Cl. .................................................. 324/309
(58) Field of Classification Search ........... 324/300–322
See application file for complete search history.

(56) References Cited

U.S. PATENT DOCUMENTS

| 4,833,407 | A | * | 5/1989 | Holland et al. | ............... 324/309 |
| 5,025,216 | A | | 6/1991 | Pauly et al. | |
| 5,122,747 | A | * | 6/1992 | Riederer et al. | ............... 324/309 |
| 5,348,011 | A | * | 9/1994 | NessAiver | ................... 600/411 |
| 5,493,224 | A | * | 2/1996 | Shiono et al. | ................. 324/309 |
| 5,671,742 | A | * | 9/1997 | Dumoulin et al. | ............. 324/318 |
| 6,472,873 | B2 | * | 10/2002 | Yamazaki | ...................... 324/309 |
| 6,965,234 | B1 | * | 11/2005 | Cunningham et al. | ......... 324/314 |
| 7,750,632 | B2 | * | 7/2010 | Qian et al. | ..................... 324/307 |
| 7,786,729 | B2 | * | 8/2010 | Chamberlain et al. | ......... 324/309 |

OTHER PUBLICATIONS

Boada, et al., "Fast Three Dimensional Sodium Imaging", Magnetic Resonance in Medicine, 1997, pp. 706-715, vol. 37.
Gatehouse, et al., Magnetic Resonance Imaging of Short T2 Components in Tissue, Clinical Radiology, 2003, pp. 1-19, vol. 58.
Glover, "Simple Analytic Spiral K-Space Algorithm", Magnetic Resonance in Medicine, 1999, pp. 412-415, vol. 42.

(Continued)

*Primary Examiner* — Dixomara Vargas
(74) *Attorney, Agent, or Firm* — Reed Smith LLP

(57) ABSTRACT

A method for producing a magnetic resonance image using an ultra-short echo time. The method includes applying a pulse sequence to an object, detecting a spirally encoded and phase encoded magnetic resonance signal associated with the object, and reconstructing the magnetic resonance image based on the spirally encoded and phase encoded magnetic resonance signal. The pulse sequence includes a slab-selective radiofrequency pulse, a slab-selective gradient pulse, a plurality of variable duration slice encoding gradient pulses, a plurality of first spiral encoding gradient pulses, and a plurality of second spiral encoding gradient pulses. The detection of the spirally encoded and phase encoded magnetic resonance signal occurs concurrently with the application of one of the plurality of first spiral encoding gradient pulses and with the application of one of the plurality of second spiral encoding gradient pulses.

18 Claims, 10 Drawing Sheets

OTHER PUBLICATIONS

Gurney, et al., "Design and Analysis of a Practical 3D Cones Trajectory", Magnetic Resonance in Medicine, 2006, pp. 575-582, vol. 55.

Heberlein, et al., "Auto-Calibrated Parallel Spiral Imaging", Magnetic Resonance in Medicine, 2006, pp. 619-625, vol. 55.

Heidemann, et al., Direct Parallel Image Reconstructions for Spiral Trajectories Using GRAPPA, Magnetic Resonance in Medicine, 2006, pp. 317-326, vol. 56.

Hoge, et al., "Density Compensation Functions for Spiral MRI", Magnetic Resonance in Medicine, 1997, pp. 117-128, vol. 38.

Idiyatullin, et al., "Fast and Quiet MRI Using a Swept Radiofrequency", Journal of Magnetic Resonance, 2006, pp. 342-349, vol. 181.

"International Standard", International Electrotechnical Commission, Second Edition, 2002, pp. 1-7.

Irarrazabal, et al., "Fast Three Dimensional Magnetic Resonance Imaging", Magnetic Resonance in Medicine, 1995, pp. 656-662, vol. 33.

Jackson, et al., "Twisting Radial Lines with Application to Robust Magnetic Resonance Imaging of Irregular Flow", Magnetic Resonance in Medicine, 1992, pp. 128-139, vol. 25.

Jackson, et al., "Selection of a Convolution Function for Fourier Inversion Using Gridding", IEEE Transactions on Medical Imaging, 1991, pp. 473-478, vol. 10. No. 3.

Larson, et al., "Designing Long-T2 Suppression Pulses for Ultrashort Echo Time Imaging", Magnetic Resonance in Medicine, 2006, pp. 94-103, vol. 56.

Mentrup, et al., "Signal Decay Correction in 2D Ultra-Short Echo Time Imaging", Magn. Reson. Mater Phy., 2006, pp. 62-70, vol. 19.

Noll, et al., "Deblurring for Non-2D Fourier Transform Magnetic Resonance Imaging", Magn. Reson. in Med., 1992, pp. 319-333, vol. 25.

Pruessmann, et al., "Advances in Sensitivity Encoding with Arbitrary κ-Space Trajectories", Magn. Reson. in Med., 2001, pp. 638-651, vol. 46.

Qian, et. al., "Decomposed Direct Matrix Inversion for Fast Non-Cartesian SENSE Reconstructions", Magn. Reson. in Med., 2006, pp. 356-363, vol. 56.

Qian, et al., "Reconstruction of MR Images From Data Acquired on an Arbitrary κ-Space Trajectory Using the Same-Image Weight", Magn. Reson. in Med., 2002, pp. 306-311, vol. 48.

Qian, et al., "Self-Calibrated Spiral SENSE", Mag. Reson. in Med., 2004, pp. 688-692, vol. 52.

Rahmer, et al., "3D Ultrashort Echo-Time Imaging of the Head", Proc. Intl. Soc. Mag. Reson. Med., 2005, p. 1074, vol. 13.

Rahmer, et al., "Three-Dimensional Radial Ultrashort Echo-Time Imaging with T2 Adapted Sampling", Mag. Reson. in Med., 2006, pp. 1075-1082, vol. 55.

Robson, et al., "Clinical Ultrashort Echo Time Imaging of Bone and Other Connective Tissues", NMR in Biomed., 2006, pp. 765-780, vol. 19.

Robson, et al., Ultrashort TE Chemical Shift Imaging (UTE-CSI), Mag. Reson. in Med., 2005, pp. 267-274, vol. 53.

Smirnov, et al., "In Vivo Cellular Imaging of Lymphocyte Trafficking by MRI: A Tumor Model Approach to Cell-Based Anticancer Therapy", Mag. Reson. in Med., 2006, pp. 498-508, vol. 56.

Sodickson, et al., "Simultaneous Acquisition of Spatial Harmonics (SMASH): Fast Imaging with Radiofrequency Coil Arrays", Mag. Reson. in Med., 1997, pp. 591-603, vol. 38.

Song, et al., "Variable TE Gradient and Spin Echo Sequences for in Vivo MR Microscopy of Short T2 Species", Mag. Reson. in Med., 1998, pp. 251-258, vol. 39.

Waldman, et al., "MRI of the Brain with Ultra-Short Echo-Time Pulse Sequences", Neuroradiology, 2003, pp. 887-892, vol. 45.

Yeh, et al., "3Parallel Magnetic Resonance Imaging with Adaptive Radius in k-Space (PARS): Constrained Image Reconstruction Using κ-Space Locality in Radiofrequency Coil Encoded Data", Mag. Reson. in Med., 2005, pp. 1383-1392, vol. 53.

Young, et al., "Magnetic Resonance: New Approaches to Imaging of the Musculoskeletal System", Physiol. Meas., 2003, pp. R1-R23, vol. 24.

Yudilevich, et al., "Spiral Sampling in Magnetic Resonance Imaging—The Effect of Inhomogeneities", IEEE Transactions on Medical Imaging, 1987, pp. 337-345, vol. MI-6 No. 4.

Takahashi, et al., "Ultra Short TE (UTE) Imaging at 8 μsec with 3D Vastly Undersampled Isotropic Projection Reconstruction (VIPR)", Proc. Intl. Soc. Mag. Reson. Med., 2005, p. 2405, vol. 13.

* cited by examiner

METHOD FOR PRODUCING A MAGNETIC RESONANCE IMAGE OF AN OBJECT HAVING A SHORT $T_2$ RELAXATION TIME

CROSS-REFERENCE TO RELATED APPLICATION

This application is a continuation of, and claims the benefit under 35 U.S.C. §120 of the earlier filing date of, U.S. patent application Ser. No. 12/054,052, filed Mar. 24, 2008, which claims the benefit under 35 U.S.C. §119(e) of the earlier filing date of U.S. Patent Application No. 60/896,465 filed on Mar. 22, 2007.

STATEMENT REGARDING FEDERALLY SPONSORED RESEARCH

This invention was made with United States Government support in the form of Grant No. R01 NS044818 from the National Institutes of Health. The United States Government may have certain rights in the invention.

BACKGROUND

This application discloses an invention which is related, generally and in various embodiments, to a method for producing a magnetic resonance image using an ultra-short echo time.

Magnetic resonance imaging (MRI) is commonly used to provide detailed images of an object (e.g., a human body). However, for objects having short $T_2$ relaxation times (e.g., $\leqq 10$ ms), images of such objects can not be properly produced by conventional MRI techniques which utilize pulse sequences with long echo times (e.g., >10 ms). Objects in the human body that have short $T_2$ relaxation times include certain tissues and superparamagnetically-labeled therapeutic cells such as, for example, cartilage, knee menisci, ligaments, tendons, cortical bone, muscles, etc.

Ultra-short echo time magnetic resonance imaging (UTE-MRI) is beginning to attract more interest due to its potential to produce images of such tissues or cells in a non-invasive manner. UTE-MRI typically employs a specialized data acquisition technique to perform MRI scans in which very short echo times (e.g., <0.5 ms) are used. The echo time (TE) is usually defined as the time period from the center (or equivalent center) of an excitation pulse to the data acquisition at the k-space center. Both short excitation pulse (~0.4 ms) and short data acquisition delay (<0.2 ms) after the excitation are pursued in UTE-MRI.

Three data acquisition techniques have traditionally been utilized with MRI to produce images of objects with short $T_2$ relaxation times. In a first technique, a split sinc pulse is used to perform two-dimensional (2D) imaging. A first half-pulse is applied with a slice-select gradient (without a refocusing lobe) and a second half-pulse is employed with an opposite sign slice-select gradient. The data from both half-excitations, which are typically collected along radial trajectories, are combined to form a full slice-select acquisition. With this technique, no refocusing lobe is required. Data acquisition can begin almost immediately (limited by the shut down time of the radio frequency (RF) hardware) after the excitation. A drawback of this technique is that split excitations may introduce artifacts caused by bulk and/or physiological motion between the two individual excitations.

In a second technique, a three-dimensional (3D) excitation using a hard pulse (i.e., a rectangular pulse) is used to image a volume instead of a slice. This technique avoids many of the problems associated with slice selections. The hard pulse excitation offers an almost immediate (limited only by hardware) data acquisition and a short excitation as well. The hard pulse has the shortest duration for a flip angle in all possible RF pulses if the amplitudes of the pulses are the same.

Without slice-select gradients, however, the hard pulse excites the entire portion of the target object within the transmit coils instead of just a selected area/volume within the coils. This leads to a field-of-view (FOV) that is passively defined by the sensitivity maps of the receiver coils. In that circumstance, a volume is imaged and a 3D radial projection imaging (PI) trajectory is usually used to collect data in k-space.

Although this technique has short readout times (~1 ms) and thus reduced signal loss, the 3D PI sampling requires a large number of radial projections in order to meet the Nyquist sampling requirement. A typical number of projections for a spatial resolution of 2 mm is approximately 31,000 which leads to a total acquisition time of about 26 minutes. The number of required projections may be reduced by partially twisting the radial trajectory. For example, by twisting each projection by 60%, the number of projections required for a spatial resolution of 2 mm is reduced by 60%, thereby decreasing the total acquisition time to about 10 minutes. The tradeoff for fewer projections in the twisted projection imaging (TPI) is the long projection arms used to maintain Nyquist sampling. A long projection arm means a long readout time (~40 ms) due to the requirement of high slew rate for efficient TPI trajectory designs. Thus, the second technique also has some drawbacks.

In a third technique, a user-defined slice is targeted by using a selective excitation pulse (e.g., a sinc pulse) and a slice-select gradient. This technique necessarily imposes a delay on data acquisitions due to its refocusing lobe. To avoid further delay of data acquisitions, variable-duration phase encodings are employed in the slice plane instead of fixed-duration phase encodings as used in most pulse sequences. The start time of data acquisition differs from one phase encoding to another and depends upon the duration of that particular phase encoding gradient. This technique results in an acquisition-weighted data collection mode, and is mainly utilized in MR microscopy and spectroscopic imaging (or chemical shift imaging) with ultra-short echo times.

Each of the above-described techniques is characterized by one or more limitations that make the techniques less than optimally suitable for imaging objects with short $T_2$ relaxation times.

SUMMARY

In one general respect, this application discloses a method for producing a magnetic resonance image using an ultra-short echo time. According to various embodiments, the method includes applying a pulse sequence to an object, detecting a spirally encoded and phase encoded magnetic resonance signal associated with the object, and reconstructing the magnetic resonance image based on the spirally encoded and phase encoded magnetic resonance signal.

The pulse sequence includes a slab-selective radiofrequency pulse, a slab-selective gradient pulse, a plurality of variable duration slice encoding gradient pulses, a plurality of first spiral encoding gradient pulses, and a plurality of second spiral encoding gradient pulses. The detection of the spirally encoded and phase encoded magnetic resonance signal occurs concurrently with the application of one of the plurality of first spiral encoding gradient pulses and with the application of one of the plurality of second spiral encoding gradient pulses.

In another general respect, this application discloses a pulse sequence for use with ultra-short echo time magnetic resonance imaging. According to various embodiments, the pulse sequence includes a first sequence of pulses and a second sequence of pulses. The first sequence of pulses includes a slab-selective radiofrequency pulse, a slab-selective gradient pulse, a first slice encoding gradient pulse having a first duration, a first spiral encoding gradient pulse, and a second spiral encoding gradient pulse. The second sequence of pulses includes a second slice encoding gradient pulse having a second duration, a third spiral encoding gradient pulse, and a fourth spiral encoding gradient pulse. The second duration is different than the first duration.

Aspects of the invention may be implemented by a computing device and/or a computer program stored on a computer-readable medium. The computer-readable medium may comprise a disk, a device, and/or a propagated signal.

BRIEF DESCRIPTION OF THE DRAWINGS

Various embodiments of the invention are described herein in by way of example in conjunction with the following figures, wherein like reference characters designate the same or similar elements.

DETAILED DESCRIPTION

It is to be understood that at least some of the figures and descriptions of the invention have been simplified to illustrate elements that are relevant for a clear understanding of the invention, while eliminating, for purposes of clarity, other elements that those of ordinary skill in the art will appreciate may also comprise a portion of the invention. However, because such elements are well known in the art, and because they do not facilitate a better understanding of the invention, a description of such elements is not provided herein.

Figure 1:
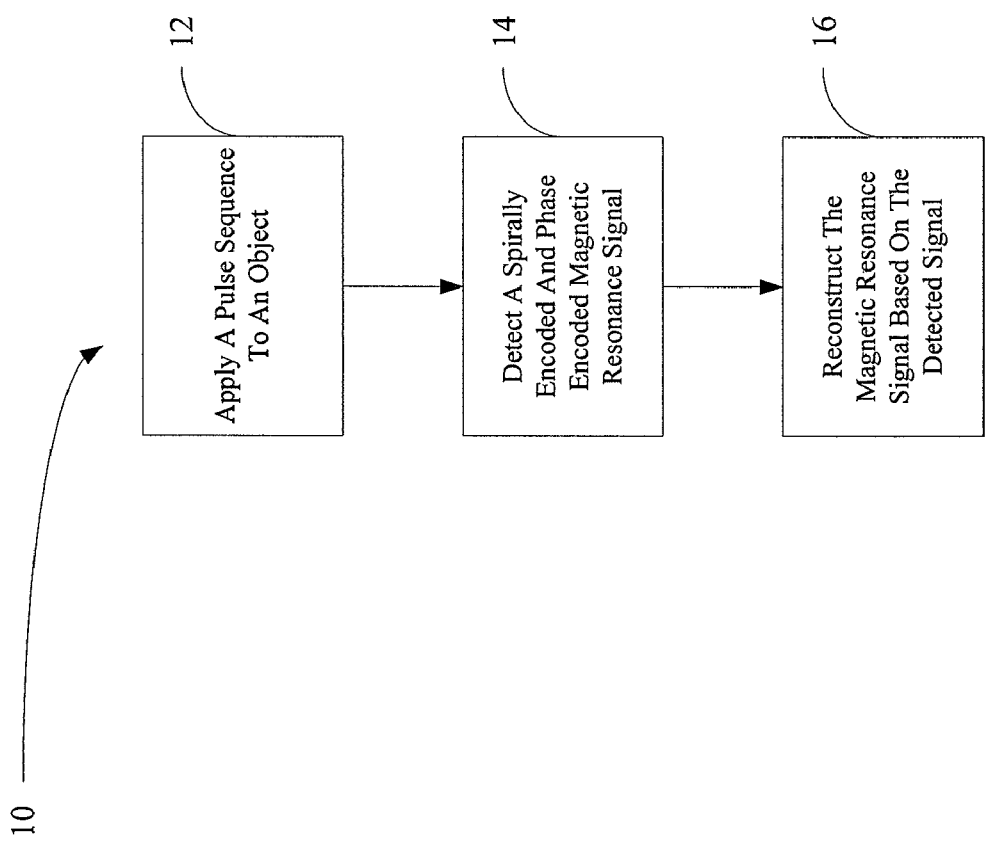
FIG. 1 illustrates various embodiments of a method for producing a magnetic resonance image using an ultra-short echo time.

FIG. 1 illustrates various embodiments of a method 10 for producing a magnetic resonance image using an ultra-short echo time. As described in more detail hereinbelow, the method may be embodied as a fast, ultra-short echo time magnetic resonance imaging method for non-invasively producing a magnetic resonance image of tissues and cells in targets with short $T_2$ relaxation times (e.g., $\leq 10$ ms).

The process begins at block 12, where a pulse sequence is applied to an object. The pulse sequence may be applied by any suitable equipment. The pulse sequence includes a slab-selective radiofrequency (RF) pulse, a slab-selective gradient pulse, a plurality of variable duration slice encoding gradient pulses, a plurality of first spiral encoding gradient pulses, and a plurality of second spiral encoding gradient pulses. The pulse sequence may be considered an acquisition-weighted stack of spirals (AWSOS) pulse sequence, and is described in more detail hereinbelow.

In general, the pulse sequence includes a series of sub-sequences, wherein each sub-sequence includes a slab-selective RF pulse, a slab-selective gradient pulse, a slice encoding gradient pulse, a first spiral encoding gradient pulse, and a second spiral encoding gradient pulse. Although each of the sub-sequences are similar, they are each different in that the duration of each of the respective slice encoding gradient pulses of the respective sub-sequences are different (the durations vary among the sub-sequences). The difference between the durations of any two of the respective slice encoding gradient pulses may not necessarily be the same as the difference between any other two of the respective slice encoding gradient pulses. According to various embodiments, the difference between the durations of first and second slice encoding gradient pulses is equal to the difference between the durations of third and fourth slice encoding pulses. According to other embodiments, the difference between the durations of first and second slice encoding gradient pulses is not the same as the difference between the durations of third and fourth slice encoding pulses.

For ease of descriptive purposes only, the pulse sequence will be described hereinafter with respect to a given sub-sequence. However, it is understood that the description is applicable to each of the sub-sequences. According to various embodiments, the slab-selective RF pulse is a symmetrical sinc RF pulse, and the slab-selective gradient pulse is of a particular amplitude. The concurrent application of the slab-selective RF pulse and the slab-selective gradient pulse is utilized to target a specific slab associated with the object. A different slab may be targeted by utilizing a slab-selective gradient pulse having an amplitude which is different than the particular amplitude.

According to various embodiments, the slice encoding gradient pulse may comprise a portion of a waveform which also includes the slab-selective gradient pulse. According to other embodiments, the waveform of the slice encoding gradient pulse may be separate from the waveform of the slab-selective gradient pulse. The application of the slice encoding gradient pulse operates to phase encode a particular slice of the slab. With the full application of the respective slice encoding gradient pulses during the successive sub-sequences, the whole slab is phase encoded completely.

According to various embodiments, each of the first and second spiral encoding gradient pulses are variable amplitude gradient pulses, and the first and second spiral encoding gradient pulses are applied concurrently. The application of the first and second spiral encoding gradient pulses operates to spirally encode a particular slice of the slab. The first spiral encoding gradient pulse may include any number of spiral interleaves, and the second spiral encoding gradient pulse may include any number of spiral interleaves. For example, according to various embodiments, the first and second spiral encoding gradient pulses may each include forty spiral interleaves. For a given sub-sequence, the combination of the application of the slice encoding gradient pulse and the first and second spiral encoding gradient pulses operates to spirally encode and phase encode a magnetic resonance signal associated with the object.

From block 12, the process advances to block 14, where the spirally encoded and phase encoded magnetic resonance signal associated with the object is detected. The signal may be detected in any suitable manner utilizing any suitable equipment. According to various embodiments, the detection of the spirally encoded and phase encoded magnetic resonance signal occurs concurrently with the application of the first and second spiral encoding gradient pulses. The detection of a magnetic resonance signal may commence anytime after a minimum time delay following the application of the slab-selective gradient pulse. According to various embodiments, the detection of a magnetic resonance signal begins prior to the start of the application of the first and second spiral encoding gradient pulses. However, for such embodiments, at least a portion of the detected magnetic resonance signal is not spirally encoded. According to other embodiments, the detection of a magnetic resonance signal begins at the start of the application of the first and second spiral encoding gradient pulses. For such embodiments, the entire magnetic resonance signal is spirally encoded and phase encoded.

From block 14, the process advances to block 16, where a magnetic resonance image is reconstructed based on the spirally encoded and phase encoded magnetic resonance signal detected at block 14. The reconstruction may be realized in any suitable manner. According to various embodiments, the reconstruction includes transforming data representative of the detected spirally encoded and phase encoded magnetic resonance signal detected to data representative of a spirally encoded magnetic resonance signal. The transformation of the data may be realized in any suitable manner. According to various embodiments, the transformation includes decomposing the three dimensional data representative of the detected spirally encoded and phase encoded magnetic resonance signal into a plurality of two dimensional data slices. For such embodiments, the decomposition may be realized by applying a discrete Fourier transform.

According to various embodiments, the reconstruction also includes producing the magnetic resonance image based on the transformed data. The production of the magnetic resonance image based on the transformed data may be realized in any suitable manner. According to various embodiments, the production includes mapping the transformed data onto Cartesian grids, and transforming the mapped data into the magnetic resonance image. The mapping of the transformed data may be realized in any suitable manner. According to various embodiments, a gridding algorithm may be utilized to map the transformed data onto Cartesian grids. The transformation of the mapped data may be realized in any suitable manner. According to various embodiments, the transformation includes applying a Fourier transform.

Figure 2:
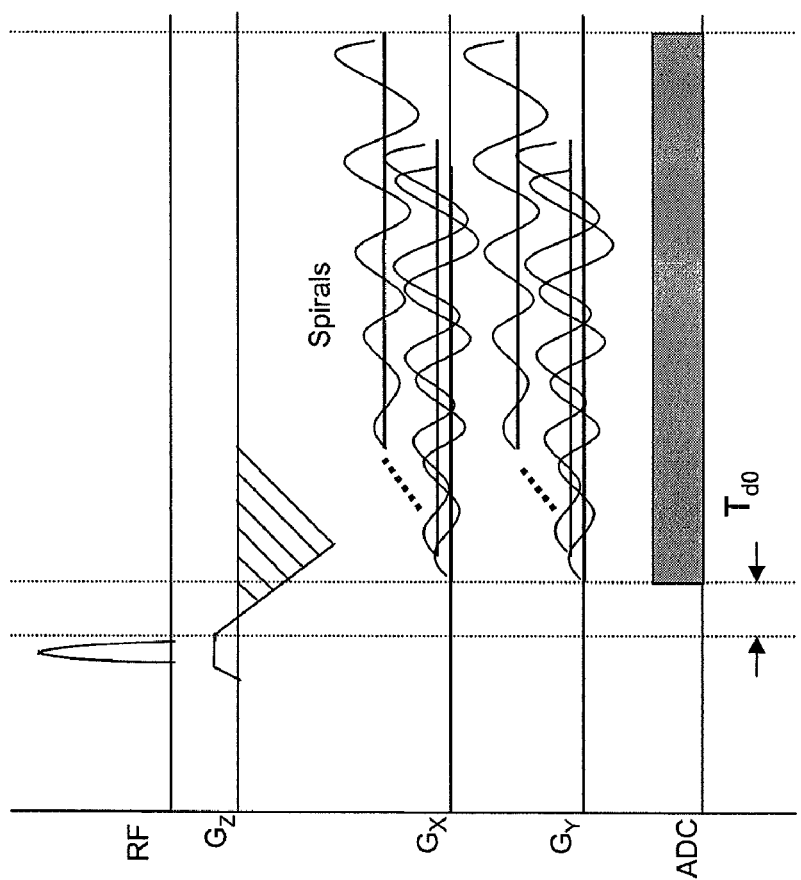
FIG. 2 illustrates various embodiments of a pulse sequence for the method of FIG. 1.

FIG. 2 illustrates various embodiments of a pulse sequence for the method of FIG. 1. The pulse sequence may be considered an acquisition-weighted stack of spirals (AWSOS) pulse sequence. As described hereinabove, the pulse sequence may be utilized to non-invasively visualize tissues and cells in targets with very short $T_2$ relaxation times (<10 ms) using magnetic resonance imaging. The pulse sequence utilizes variable-duration slice encodings and movable spiral data collections to minimize $T_2$-induced signal decay. The pulse sequence is designed to allow the acquisition of a three dimensional (3D) raw data set with phase encoding in the slice direction but spiral encoding within the slice plane. The pulse sequence allows the sampling of the k-space in a cylindrical volume in order to separate in-plane resolution from slice thickness and utilizes spiral trajectories to decrease the number of excitations needed to satisfy the Nyquist sampling requirement.

Any part of the human body or any organ in the body can be the scanning target of the pulse sequence if a corresponding transmit/receive coil(s) is available. Moreover, the pulse sequence may be utilized with both proton and non-proton MRI, and may be implemented via clinical MRI scanners with main magnetic fields of at least 1.5T. For better signal-to-noise ratio (SNR), a higher field ($\leq$3T) MRI scanner is recommended for non-proton MRI.

In FIG. 2, the slab-selective radiofrequency pulse is represented by the waveform (RF) which is a half-cycle sine radiofrequency pulse, the slab-selective gradient pulse and the plurality of variable duration slice encoding gradient pulses are collectively represented by the waveform ($G_z$), the plurality of first spiral encoding gradient pulses are represented by the waveform ($G_x$), and the plurality of second spiral encoding gradient pulses are represented by the waveform ($G_y$). The slab-selective radiofrequency pulse is used to excite a slab of thickness h, which is defined by the slab-selective gradient pulse. The amplitude $G_0$ of the slab-selective gradient pulse is related to the slab thickness (h) as shown in Equation 1.

$$G_0 = \frac{4\eta_c}{\gamma h \tau_{rf}} \qquad \text{Equation 1}$$

where the sinc cycle is $\eta_c$, the duration is $\tau_{rf}$, and the gyromagnetic ratio is $\gamma$ in Hz/T.

The minimum echo time ($t_e$) corresponding to this type of excitation is well-known to be given by Equations 2a-2c.

$$t_e = 0.5\tau_{rf} + t_1 + 2t_2 \qquad \text{Equation 2a}$$

$$t_1 = G_0/S_{max} \qquad \text{Equation 2b}$$

$$t_2 = [0.5 t_1(\tau_{rf} + t_1)]^{1/2}, w/t_2 S_{max} < G_{max} \qquad \text{Equation 2c}$$

where $G_{max}$ and $S_{max}$ are the maximum amplitudes of the slab-selective gradient pulse and slew rate of the MRI system, respectively. The optimization of the rf pulse duration $\tau_{rf}$, the slab thickness h, and the minimum echo time $t_e$ can therefore be implemented using Equations 1 and 2.

As shown in FIG. 2, the variable durations of the respective slice encoding gradient pulses lead to a variable delay of the spiral encoding gradient pulses, and data acquisition (ADC) may commence at the minimum time delay $T_{d0}$ or at the starting time of individual spiral encoding gradient pulses. Oblique slice encoding is obtained by rotating the logical gradients ($G_x$, $G_y$, and $G_z$).

Figures 3A, 3B:
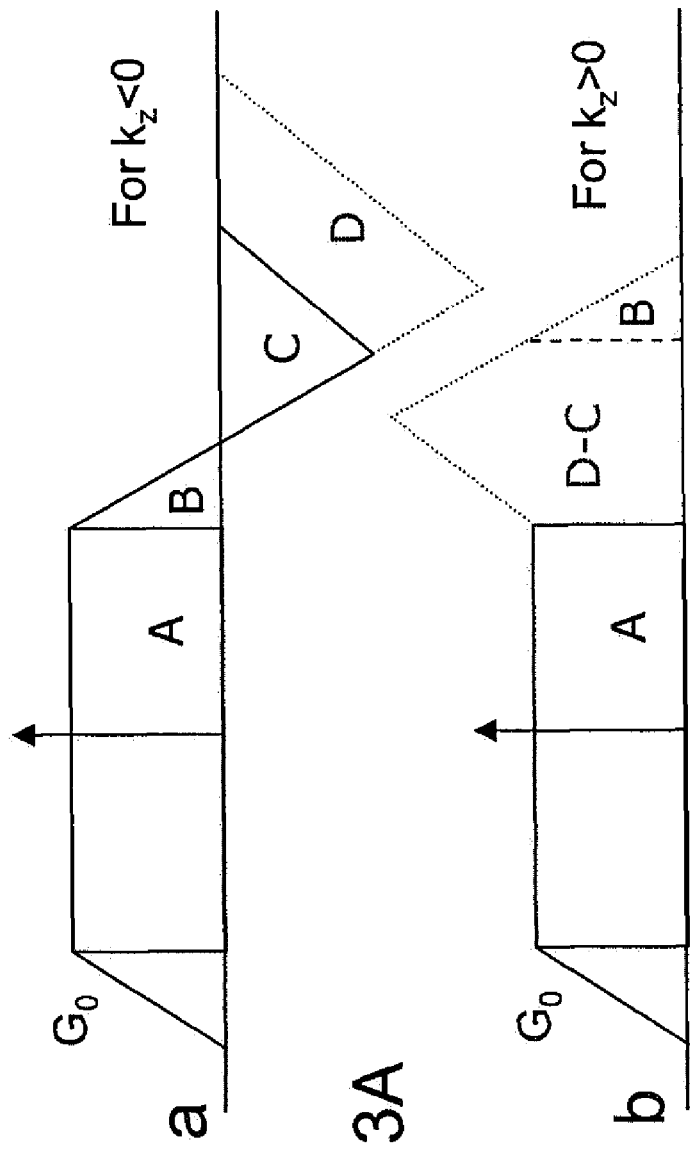
FIG. 3A illustrates various embodiments of a phase encoding gradient waveform utilized with various embodiments of the pulse sequence of FIG. 2.
FIG. 3B illustrates various embodiments of a phase encoding gradient waveform utilized with various embodiments of the pulse sequence of FIG. 2.

FIGS. 3A and 3B illustrate various embodiments of phase encoding gradient waveforms utilized with various embodiments of the pulse sequence of FIG. 2. FIG. 3A details a slice encoding gradient pulse with variable duration for negative $k_z$, and FIG. 3B details a slice encoding gradient pulse with variable duration for positive $k_z$. In the figures, area A is the area of the half constant, and area B is the decay ramp of the slab-selective gradient pulse. Area C is the refocusing area and is equal in size to area A plus area B.

As shown in FIG. 3A, the slice encoding gradient pulse overlaps on the decay ramp of the slab-selective gradient pulse and occurs right after the constant segment of the slab-selective gradient pulse. The waveform of the slice-encoding gradient pulse is characterized by Equations 3-5 (below) and FIG. 3A. The areas of the half constant and decay ramp of the slab-selective gradient pulse, represented by area A and area B, respectively, is balanced by the refocusing area C:

$$C = A + B = (1/2) G_o (\tau_{rf} + \tau_{decay})$$ Equation 3 with the decay-ramp duration $\tau_{decay}$. For a slice-encoding step $k_z$, the corresponding area (D) is defined by Equation 4.

$$D = |k_z|/\gamma$$ Equation 4

In FIG. 3A, area D corresponds to a $k_z$. If area D is less than area C in FIG. 3B, then the slice encoding is switched to FIG. 3A. The total slice encoding area (E) resulting from area C and area D is given by Equations 5a-5c.

$$E = C + D, k_z < 0 \text{ (FIG. 2A waveform)}$$ Equation 5a $$E = C - D, k_z > 0, D \leq C \text{ (FIG. 2A waveform)}$$ Equation 5b $$E = D - C, k_z > 0, D > C \text{ (FIG. 2B waveform)}$$ Equation 5c The duration and amplitude of the resultant slice-encoding gradient pulse can be calculated from the area E associated waveforms in FIGS. 3A and 3B. An example of this gradient waveform is shown in FIG. 4, which is a chart of amplitude versus duration of phase encoding for variable-duration slice-encoding gradient waveforms utilized with various embodiments of the pulse sequence of FIG. 2.

Figure 4:
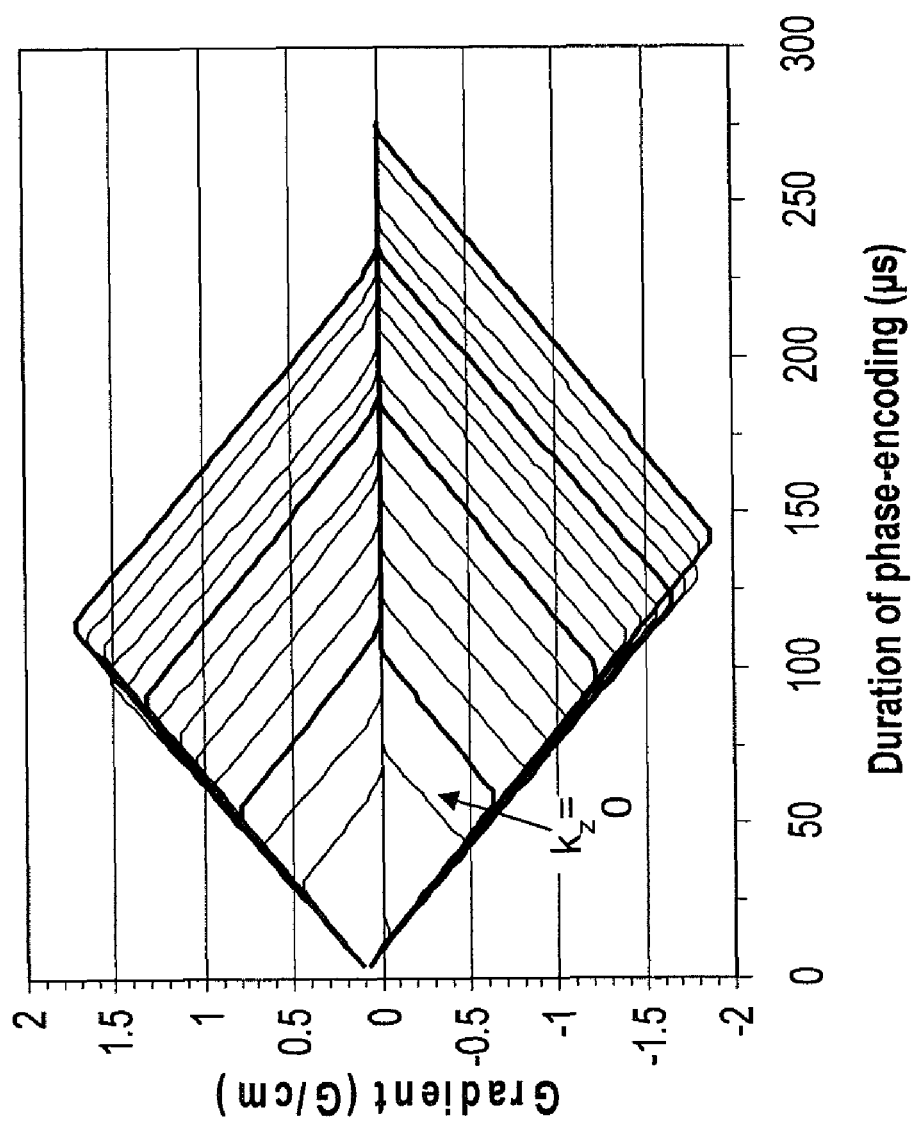
FIG. 4 is a chart of amplitude versus duration of phase encoding for variable-duration slice-encoding gradient waveforms utilized with various embodiments of the pulse sequence of FIG. 2.

Specifically, FIG. 4 shows exemplary waveforms of a variable-duration slice-encoding gradient pulses for both negative and positive $k_z$ values ($G_0 = 0.3$ G/cm, $\Delta k = 1/15$ cm$^{-1}$, encoding steps=30). The duration varies non-uniformly from one encoding step to another, and the minimum duration (52 μs) occurs at $k_z = \Delta k$ due to the superimposed refocusing lobe. If the amplitude is larger than the available gradient $G_{max}$ of the system, the triangular waveform shown in FIG. 3A, FIG. 3B or FIG. 4 may be replaced with a trapezoidal waveform.

With respect to data acquisition, the readout of the magnetic resonance signal corresponding to the pulse sequence may commence immediately after the application of a slice encoding gradient pulse. The excited spins in a target object are spatially encoded by two time-varying spiral encoding gradient pulses in a plane perpendicular to the slice direction (e.g., $G_x$ and $G_y$). The variable duration of the respective slice-encoding gradient pulses leads to variable commencing of the application of the spiral encoding gradient pulses.

Figure 5:
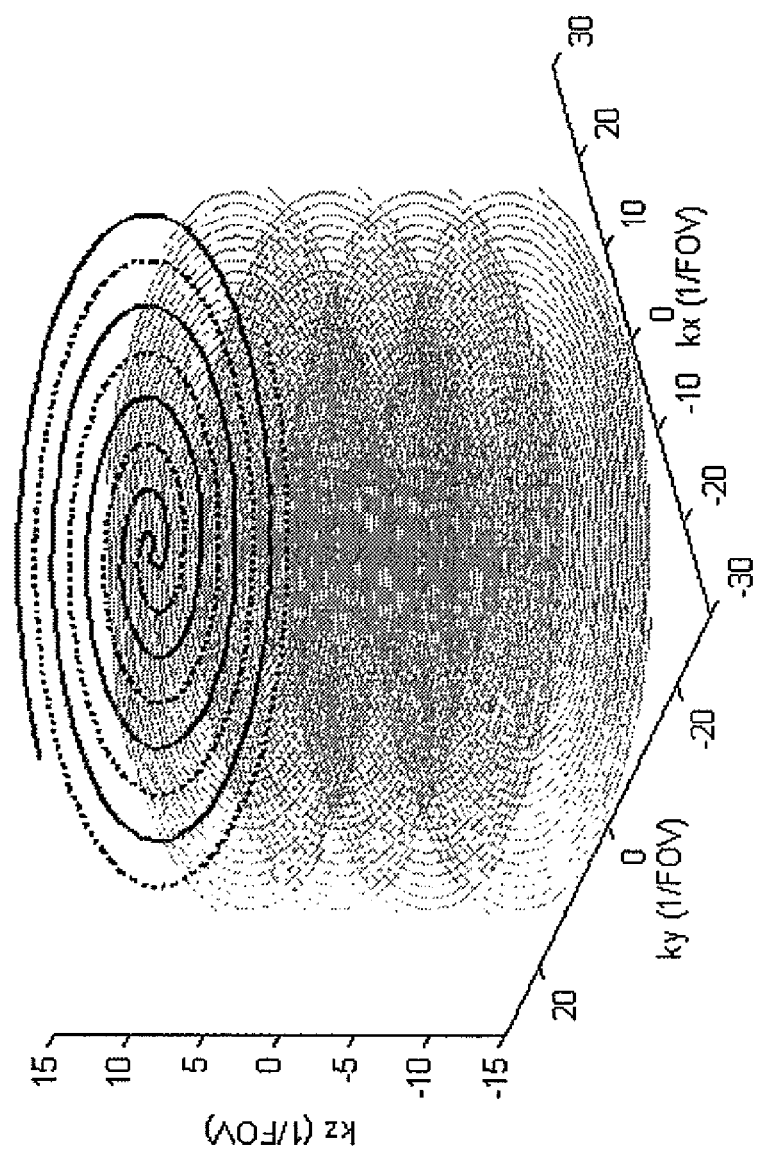
FIG. 5 illustrates various embodiments of a stack of spirals trajectory utilized with various embodiments of the pulse sequence of FIG. 2.

FIG. 5 illustrates various embodiments of a stack of spirals trajectory utilized with various embodiments of the pulse sequence of FIG. 2. As shown in FIG. 5, a stack of spirals is formed in the k-space after all slice encodings are completed. FIG. 5 details the stack of spirals sampling in k-space within a cylinder used to image a volume. Each specific imaging plane includes interleaved spirals (alternating solid and dashed lines in FIG. 5) in the $k_x$-$k_y$ plane. A "stack" of these interleaved spirals may be uniformly stacked along the $k_z$ direction to fill the entire imaging volume (e.g., cylinder). This $k_z$ direction is referred to herein as being perpendicular to the imaging plane ($k_x$, $k_y$).

The pulse sequence allows the sampling of a k-space in a cylindrical volume with its symmetrical axis in the slice direction (i.e., $k_z$ direction). A uniform or non-uniform sampling in the $k_z$ direction may be performed within $-k_{z,max} \leq k_z < k_{z,max}$, where the maximum $k_z$ value is determined by the slice thickness $\Delta z$ (i.e., the spatial resolution in the slice direction) and $k_{z,max} = 1/(2\Delta z)$. The slice-encoding increment $\Delta k_z$ is determined by the slab thickness h and $\Delta k_z = 1/h$.

Using these parameters, a "disk-shaped" area may be sampled along spiral trajectories in the $k_x$-$k_y$ plane at each $k_z$, and all the disks together constitute a stack of such spirals as shown in FIG. 5. The radius of each disk is the maximum value of $k_x$ (or $k_y$) in the $k_x$-$k_y$ plane, which is defined by the in-plane resolution $\Delta x$ (or $\Delta y$) and $k_{x,max} = 1/(2\Delta x)$. The separation of slice thickness ($\Delta z$) from the in-plane resolution ($\Delta x$) in the data representative of the spirally encoded and phase encoded magnetic resonance signal offers an opportunity to enhance the in-plane resolution while the slice thickness remains unchanged. As a comparison, existing 3D radial sampling methods produce an isotropic spatial resolution ($\Delta x = \Delta y = \Delta z$) in all the three directions, which requires a longer acquisition time and suffers lower signal-to-noise ratio (SNR) when a higher resolution is pursued as compared to the method 10 of FIG. 1.

As described hereinabove, the reconstruction of the magnetic resonance image may be realized in any suitable manner. According to various embodiments, the reconstruction process is essentially a two step process. First, a discrete Fourier transformation (DFT) or fast Fourier transformation (FFT) is performed in the $k_z$ direction (perpendicular to the imaging plane) to decompose data representative of the detected spirally encoded and phase encoded magnetic resonance signal from 3D to 2D. Then a gridding algorithm is employed to reconstruct images from the spirally encoded data sets for each of the 2D data sets.

According to various embodiments, for the decomposition of 3D data into multiple 2D data sets, one-dimensional (1D) Fourier transformation (FT) is performed in the slice encoding ($k_z$) direction. Highly accurate sampling density compensation may be utilized before the FT implementation if non-uniform slice encodings are performed. In essence, this step takes the "cylindrically" collected stack of spirals data and decomposes it in a series of in-plane 2D data sets that may be further processed into images.

After decomposition, a subsequent gridding algorithm may then employed to reconstruct images from the spiral data sets for each of the acquired slices. If the density compensation is utilized for the spiral sampling, the density compensation is performed before the gridding of the spiral data onto Cartesian grids. This step generally processes the spiral-based slice data in each of the image planes and maps this data into a Cartesian coordinate system that is used to display each of the slice images (or a combined 3D image) of the target object for the end user.

Figure 6:
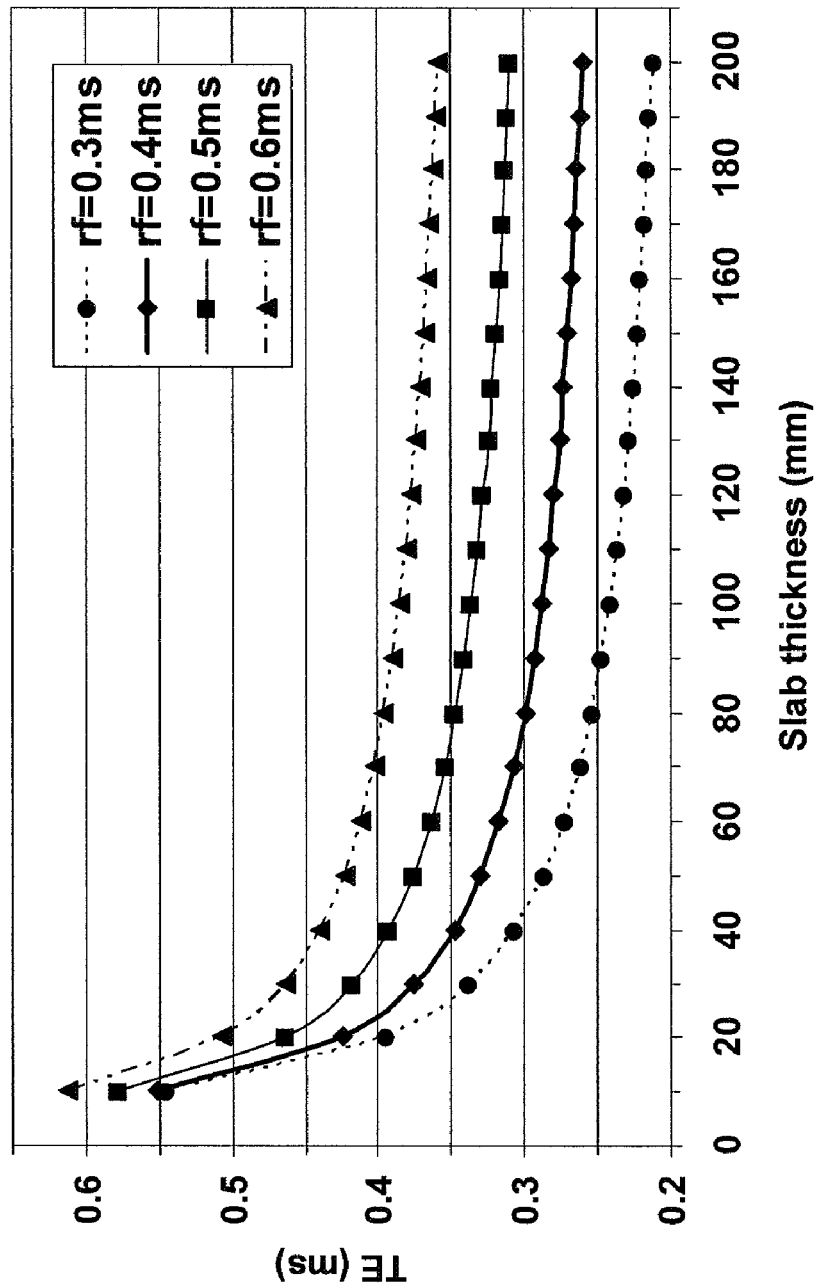
FIG. 6 is a chart of the echo time versus the slab thickness for a variety of RF durations according to various embodiments.

FIG. 6 is a chart of the echo time (TE) versus the slab thickness for a variety of RF durations according to various embodiments. The minimum echo time in the pulse sequence depends upon the duration of the slab-selective radiofrequency pulse and the length of the "slab" to be excited. This is, of course, in addition to the limitations inherent in the hardware itself (e.g., the maximum slab-selective gradient pulse and slew rate, the coil switching time from transmit to receive mode, the synchrony of the pulses, etc.). These echo times shown in FIG. 6 are based on a sinc rf pulse of half cycles on a clinical MRI system ($G_{max} = 40$ mT/m and $S_{max} = 150$ mT/m/ms).

As shown in FIG. 6, for these embodiments, the echo time decreases regularly with slab thickness for all rf pulse durations. Notably, the echo time decreases dramatically (~50%) when the slab extends from 1 cm to 7 cm, but the echo time decreases to a much smaller extent as the slab thickness increases beyond 7 cm. The echo time, on the other hand, increases linearly with excitation duration for most slabs, but does so in a non-linear fashion for very short slabs (e.g., 1-3 cm).

In general, decreasing the duration of the applied excitation pulse is an efficient way in which to produce short echo times, but this may be limited by the safety requirements on clinical scanners. Consequently, both excitation duration and slab thickness may be optimized together in order to produce the shortest feasible echo time. The chart of FIG. 6 may be utilized as a guide for achieving such optimization. For example, to produce a typical echo time of 0.4 ms, the minimum slab thickness is approximately 2 cm for a 0.3 ms rf pulse, 2.5 cm for a 0.4 ms pulse, and 7 cm for a 0.6 ms rf pulse duration.

Figure 7A:
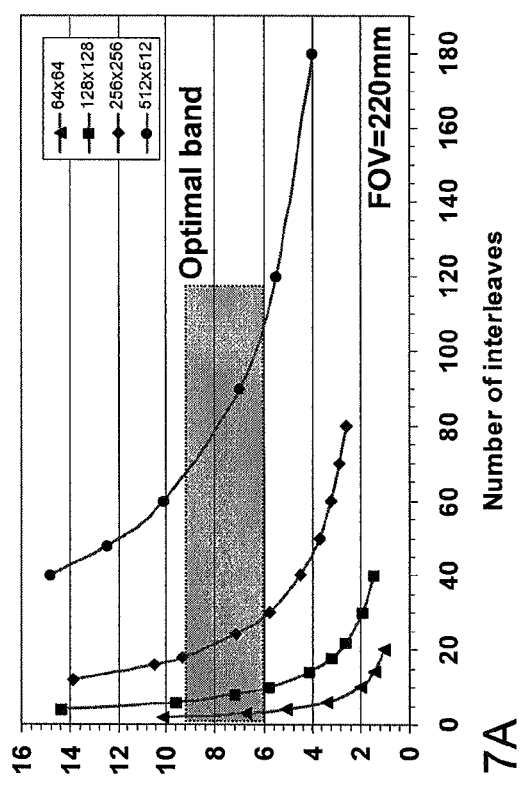
FIG. 7A is a chart of the readout times versus the number of spiral interleaves according to various embodiments.
Figure 7B:
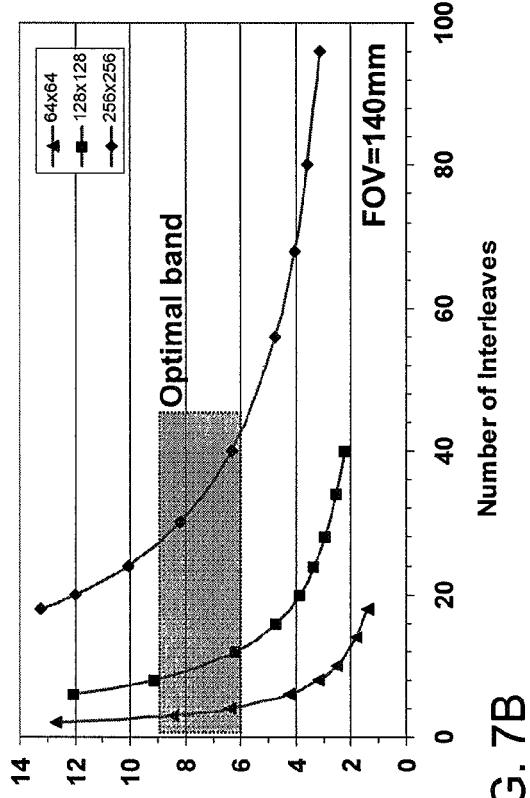
FIG. 7B is a chart of the readout times versus the number of spiral interleaves according to other embodiments.

FIG. 7A is a chart of the readout times versus the number of spiral interleaves according to various embodiments, and FIG. 7B is a chart of the readout times versus the number of spiral interleaves according to other embodiments. FIG. 7A is for a field-of-view (FOV) of 22 cm and FIG. 7B is for a field-of-view (FOV) of 14 cm. The number of spiral interleaves determines the readout time of an individual interleaf, and more interleaves lead to a shorter readout time. For FIGS. 7A and 7B, the optimal band for the readout time is between 6 and 9 ms when the typical $T_2$ relaxation time of an object is 3 ms.

The optimal readout time of 2-3 $T_2$ is clinically tolerable in ultra-short TE MRI (e.g., 6-9 ms for a typical short $T_2$ of 3 ms). For the embodiments corresponding to FIG. 7A, the optimal numbers of interleaves are shown as being: 2-4 for a matrix size 64×64; 6-10 for a matrix of 128×128; 18-30 for a matrix of 256×256; and 50-120 for a matrix of 512×512, all at a FOV of 22 cm. For the embodiments corresponding to FIG. 7B, where the FOV is compressed down to 14 cm, the optimal numbers of interleaves are shown as being: 3-4 for a matrix size of 64×64; 8-12 for a matrix of 128×128; and 24-40 for a matrix of 256×256. The total acquisition time for the embodiments corresponding to FIGS. 7A-B (TR=100 ms and slice-encodings=30) can be as short as 54 seconds for an in-plane resolution of 0.86 mm at a FOV of 22 cm, or it can be 72 seconds for an in-plane resolution of 0.55 mm at a FOV of 14 cm. The total acquisition time may be further decreased by utilizing fewer phase encodings for shorter slabs.

Figures 8A, 8B, 8C:
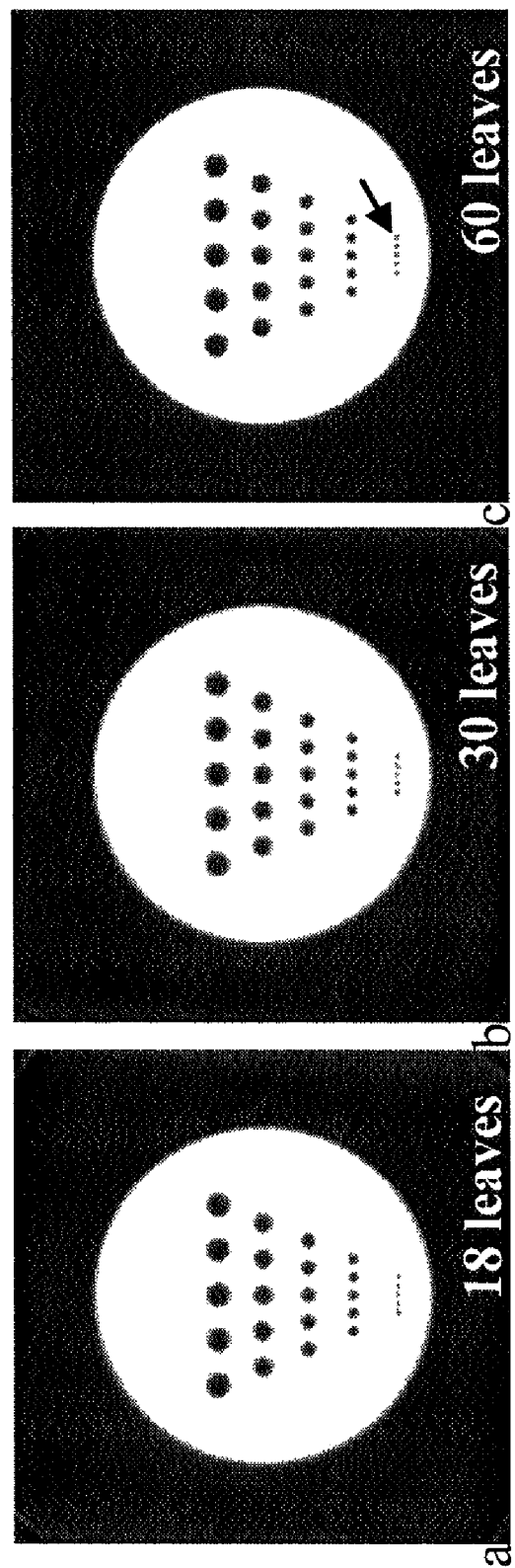
FIGS. 8A-8C illustrate images produced by computer simulations of various embodiments of the pulse sequence of FIG. 2.

FIGS. 8A-8C illustrate images produced by computer simulations of various embodiments of the pulse sequence of FIG. 2. The images are of a cylinder (16 cm length×15 cm diameter, $T_2$=3 ms) with varying diameter rods inside the cylinder. The rods were arranged in 5 rows with diameters of 0.2 cm, 0.4 cm, 0.6 cm, 0.8 cm and 1.0 cm from bottom to top, respectively. The k-space data including $T_2$ decay during the slice encodings and spiral readouts were analytically calculated along the spiral trajectories with a sampling interval of 4 μs.

The simulations were performed for a variety of different numbers of interleaves ($T_2$=3 ms, FOV=22 cm, matrix size of 256×256). FIG. 8A utilizes 18 leaves; FIG. 8B utilizes 30 leaves; and FIG. 8C utilizes 60 leaves. The $T_2$-induced signal decay was illustrated with three different readout times from 3-fold of $T_2$ (FIG. 8A), to 2-fold of $T_2$ (FIG. 8B) and $T_2$ (FIG. 8C).

The simulations confirmed the expected outputs resulting from the application of the pulse sequence in that even the smallest 0.2 cm rods had recognizable clarity. The image blurring caused by the $T_2$-induced signal decays during the spiral readouts was improved when the number of interleaves was increased (or when the readout time was decreased). Looking at the lowest row of simulated rods (the smallest rods), it is shown that the image blurring is improved as the readout time decreases from left to right in the drawings (see arrow in FIG. 8C).

Additional simulations/experiments on phantoms and human subjects were performed on a 3T clinical scanner ($G_{max}$=40 mT/m, $S_{max}$=150 mT/m/ms) using a standard head coil. A sine pulse of 0.4 ms duration and 0.5 cycles was used to excite a slab of 15 cm in length. There were 30 slice encodings to obtain a thickness of 5 mm. Different in-plane resolutions were used to evaluate the merits of the pulse sequence.

Figures 9A, 9B, 9C:
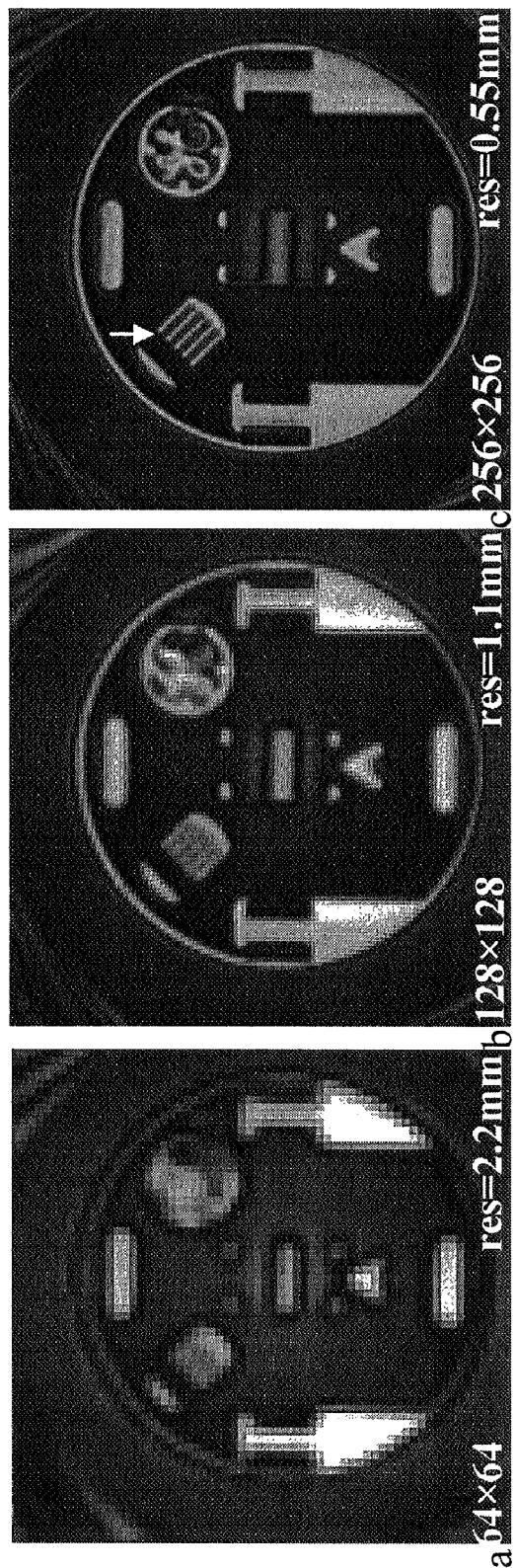
FIGS. 9A-9C illustrate phantom images produced by various embodiments of the pulse sequence of FIG. 2.
Figures 10A, 10B, 10C, 10D, 10E, 10F:
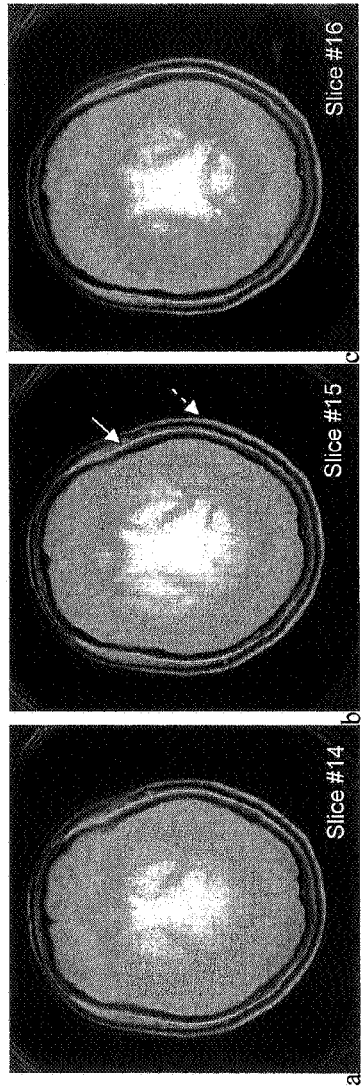
FIGS. 10A-10F illustrate human brain images produced by various embodiments of the pulse sequence of FIG. 2.

FIGS. 9A-9C illustrate phantom images produced by various embodiments of the pulse sequence of FIG. 2. The phantom images are shown at three different spatial in-plane resolutions but at the same slice thickness. The images are exemplary AWSOS proton phantom images with TE/TR=0.408/100 ms and FOV=14×14×15 $cm^3$ for a variety of different matrix sizes. For example, FIG. 9A was produced with a matrix size of 64×64×30, FIG. 9B was produced with a matrix size of 128×128×30, and FIG. 9C was produced with a matrix size of 256×256×30.

The AWSOS pulse sequence was utilized to produce a high in-plane resolution of 0.55 mm when the matrix size was increased to 256×256. The other two lower in-plane resolutions (1.1 mm and 2.2 mm), achieved at matrix sizes of 128×128 and 64×64, respectively, demonstrate the flexibility of the AWSOS pulse sequence to meet different requirements on spatial resolutions. As indicated by the inset arrow in FIG. 9C, the high in-plane resolution realized with these embodiments allows for the recognition of the specific bars in the detailed comb.

FIGS. 10A-10F illustrate human brain images produced by various embodiments of the pulse sequence of FIG. 2. The images detail successive slices from exemplary AWSOS proton brain images with TE/TR=0.408/1000 ms, FOV=22×22× 15 $cm^3$ and a matrix size of 256×256×30. The slices were selected from the central part of the excited slab (centered at slice #15 in FIG. 10B). The resolution at the displayed central slices was 0.86×0.86×5 $mm^3$.

The AWSOS pulse sequence was utilized to produce a high in-plane resolution of 0.86 mm and the images clearly show the small structures of white/gray matters. In addition, due to ultra-short TE (0.408 ms) used in this experiment, the signal from the meninges (solid arrow in FIG. 10B) under the skull was significantly enhanced and was as strong as the signal from the scalp (dashed arrow in FIG. 10B) even though no fat saturation was performed during the data acquisitions. Again, the high in-plane resolution of the scan makes very small internal structures clearly visible in the reproduced image and demonstrates the wide variety of uses for ultra-short echo time MRI in the disease diagnosis and treatments monitoring of the human brain.

Nothing in the above description is meant to limit the invention to any specific materials, geometry, or orientation of elements. Many part/orientation substitutions are contemplated within the scope of the invention and will be apparent to those skilled in the art. The embodiments described herein were presented by way of example only and should not be used to limit the scope of the invention.

Although the invention has been described in terms of particular embodiments in this application, one of ordinary skill in the art, in light of the teachings herein, can generate additional embodiments and modifications without departing from the spirit of, or exceeding the scope of, the claimed invention. Accordingly, it is understood that the drawings and the descriptions herein are proffered only to facilitate comprehension of the invention and should not be construed to limit the scope thereof.

What is claimed is:

1. A method, implemented at least in part by a magnetic resonance imaging scanner, for producing a magnetic resonance image of an object having a short $T_2$ relaxation time, the method comprising:
   with the magnetic imaging scanner, applying a pulse sequence to the object, wherein the pulse sequence comprises:
      a slab-selective radiofrequency pulse;
      a slab-selective gradient pulse;
      a plurality of variable duration slice encoding gradient pulses;
      a plurality of first encoding gradient pulses; and
      a plurality of second encoding gradient pulses, wherein the first and second gradient pulses are one of the following:
         spiral encoding gradient pulses; and
         spiral-like encoding gradient pulses;
   detecting a magnetic resonance signal associated with the object, wherein the detection of the magnetic resonance signal occurs concurrently with:
      the application of one of the plurality of first encoding gradient pulses; and
      the application of one of the plurality of second encoding gradient pulses; and
   reconstructing the magnetic resonance image based on the magnetic resonance signal.

2. The method of claim 1, wherein applying the pulse sequence comprises applying a radiofrequency pulse of a symmetrical sinc waveform.

3. The method of claim 1, wherein applying the pulse sequence comprises applying a radiofrequency pulse of an arbitrary waveform.

4. The method of claim 1, wherein applying the pulse sequence comprises:
   applying the slab-selective radiofrequency pulse; and
   applying the slab-selective gradient pulse concurrently with the application of the slab-selective radiofrequency pulse.

5. The method of claim 1, wherein applying the pulse sequence comprises:
   applying a first one of the plurality of variable duration slice encoding gradient pulses, wherein the first one has a first duration; and
   applying a second one of the plurality of variable duration slice encoding gradient pulses, wherein the second one has a second duration, and wherein the second duration is different than the first duration.

6. The method of claim 5, wherein applying the pulse sequence further comprises applying a third one of the plurality of variable duration slice encoding gradient pulses, wherein the third one has a third duration, and wherein the third duration is different than the first and second durations.

7. The method of claim 6, wherein a difference between the first and second durations is equal to a difference between the second and third durations.

8. The method of claim 6, wherein a difference between the first and second durations is different than at least one of the following:
   a difference between the first and third durations; and
   a difference between the second and third durations.

9. The method of claim 1, wherein applying the pulse sequence comprises:
   applying one of the plurality of first encoding gradient pulses; and
   applying one of the plurality of second encoding gradient pulses concurrently with the application of the one of the plurality of first encoding gradient pulses.

10. The method of claim 1, wherein reconstructing the magnetic resonance image comprises:
    transforming data representative of the magnetic resonance signal to data representative of a non-phase encoded magnetic resonance signal; and
    producing the magnetic resonance image based on the transformed data.

11. The method of claim 10, wherein transforming the data comprises decomposing three dimensional data into a plurality of two-dimensional data slices.

12. The method of claim 11, wherein decomposing the data comprises applying a discrete Fourier transform.

13. The method of claim 10, wherein producing the magnetic resonance image based on the transformed data comprises:
    mapping the transformed data onto Cartesian grids; and
    transforming the mapped data into the magnetic resonance image.

14. The method of claim 13, wherein transforming the mapped data comprises applying a Fourier transform.

15. A method, implemented at least in part by a magnetic resonance imaging scanner, for producing a magnetic resonance image of an object having a short $T_2$ relaxation time, the method comprising:
    with the magnetic imaging scanner,
       exciting a slab of the object;
       phase-encoding a slice of the slab; and
       further encoding the phase-encoded slice; wherein further encoding the phase-encoded slice comprises:
          applying a first encoding gradient pulses to the object; and applying a second encoding gradient pulse to the object, wherein the first and second encoding gradient pulses are one of the following: spiral encoding gradient pulses; and spiral-like encoding gradient pulses;
    detecting a magnetic resonance signal associated with the object, wherein the detection of the magnetic resonance signal occurs concurrently with the further encoding of the phase-encoded slice; and
    reconstructing the magnetic resonance image based on the magnetic resonance signal.

16. The method of claim 15, wherein exciting the slab comprises:
    applying a slab-selective radiofrequency pulse to the object; and
    applying a slab-selective gradient pulse to the object concurrently with the application of the slab-selective radiofrequency pulse.

17. The method of claim 15, wherein phase-encoding the slice of the slab comprises applying a variable duration slice encoding gradient pulse to the object.

18. The method of claim 15, wherein reconstructing the magnetic resonance image comprises:
    transforming data representative of the magnetic resonance signal to data representative of a non-phase encoded magnetic resonance signal; and
    producing the magnetic resonance image based on the transformed data.

* * * * *